United States Patent [19]

Hahn et al.

[11] 4,324,939
[45] Apr. 13, 1982

[54] PROCESS FOR PREPARING REACTION PRODUCTS OF CONJUGATED DIOLEFINS AND AROMATIC HYDROCARBONS

[75] Inventors: Karl Hahn, Marl; Wolfgang Kampf, Haltern, both of Fed. Rep. of Germany

[73] Assignee: Chemische Werke Huels, AG, Marl, Fed. Rep. of Germany

[21] Appl. No.: 223,618

[22] Filed: Jan. 9, 1981

[30] Foreign Application Priority Data

Jan. 10, 1980 [DE] Fed. Rep. of Germany ....... 3000708

[51] Int. Cl.$^3$ ............................................. C07C 3/00
[52] U.S. Cl. ............................... 585/438; 252/429 B; 252/431 C; 252/431 P
[58] Field of Search .................... 585/438; 252/429 B, 252/431 P, 431 C

[56] References Cited

U.S. PATENT DOCUMENTS

| | | | |
|---|---|---|---|
| 3,953,535 | 4/1976 | Shima et al. | 585/438 |
| 3,954,668 | 5/1976 | Yoo et al. | 252/431 P |
| 4,034,052 | 7/1977 | Puskas | 585/438 |

*Primary Examiner*—Arthur P. Demers
*Attorney, Agent, or Firm*—Millen & White

[57] ABSTRACT

A process for preparing a reaction product of a conjugated diolefin and an aromatic hydrocarbon comprises contacting these reactants with a catalyst comprising
(1) a phosphorous modified cobalt compound comprising a cobalt compound which is soluble in the aromatic hydrocarbon and a phosphorous compound of the formula

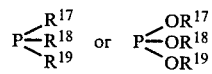

wherein $R^{17}$, $R^{18}$ and $R^{19}$ each, independently, is $C_{1-14}$-alkyl, $C_{2-14}$-alkenyl or $C_{6-14}$-aryl
(2) a halogen-containing organoaluminum compound; and
(3) a modifier of the formula

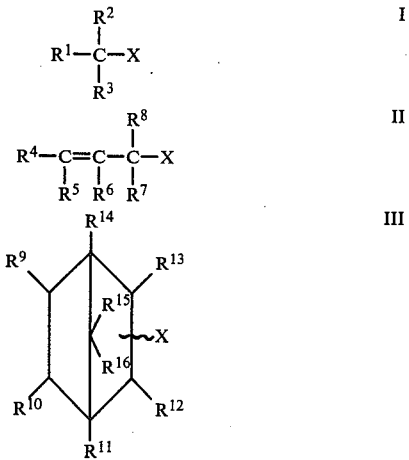

wherein
X is chlorine, bromine, or iodine, and
$R_1$ through $R^{16}$, independently, are
straight-chain or branched, saturated or unsaturated, aliphatic or cycloaliphatic hydrocarbon radicals of 1–20 carbon atoms, optionally substituted by 1–41 halogen atoms, or hydrocarbon aryl radicals of 6–14 carbon atoms optionally substituted by (a) 1–5 straight-chain or branched, saturated or unsaturated, aliphatic or cycloaliphatic hydrocarbon radicals each of 1–10 carbon atoms, each optionally halogen-substituted, or (b) 1–9 halogen atoms, and wherein $R^4$ through $R^{16}$ can also be hydrogen, and $R^2$ and $R^3$ can also be hydrogen only when $R^1$ is optionally substituted hydrocarbon aryl as defined above.

12 Claims, No Drawings

PROCESS FOR PREPARING REACTION PRODUCTS OF CONJUGATED DIOLEFINS AND AROMATIC HYDROCARBONS

BACKGROUND OF THE INVENTION

The alkenylation of aromatic hydrocarbons by dienes has been described repeatedly in the literature (inter alia: G. O. Olah, Friedel-Crafts and Related Reactions, vol. II/1). This preparation takes place using homogeneous and heterogeneous acidic catalysts, producing predominantly alkenyl and/or dialkenyl derivatives of aromatic hydrocarbons of the formulae

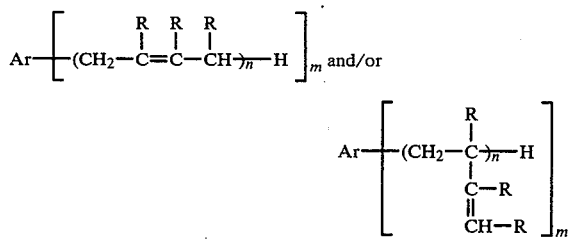

wherein
Ar is an aryl residue,
the residues R, independently of one another, are hydrogen or alkyl, and
n and m each are 1 or 2.

Such products heretofore were only of relatively low interest and frequently had the character of undesirable by-products. Due to their high proportion of trans-double bonds, they possessed poor air-drying properties and furthermore were relatively readily volatile. Longer-chain telomers (n>2) are normally produced only to a minor extent.

Products having longer side chains can be obtained by following the methods of German Pat. No. 1,137,727 and German Pat. No. 1,170,932. They, too, contain primarily trans-double bonds and, in all cases, a considerable proportion of undesirable, readily volatile monoalkenylation products (see also H. Weber and B. Schleimer, "Brennstoff-Chemie" [Fuel Chemistry] 49:329 et seq. [1968]). They have been proposed for use in modification of elastomeric and thermoplastic synthetic resins, of lubricants and, after hydrogenation, of detergent raw materials.

Using catalysts from Cr(III) halides and alkyl aluminum halides according to the process of U.S. Pat. No. 3,373,216, products are obtained, having a trans-content which has been reduced (35–80%). However, they contain only minor proportions of incorporated aromatics.

Japanese Laid-Open Application No. 49-32985 describes a process for the preparation of polymers containing aromatic hydrocarbons on a polydiene chain (incorporation takes place probably statistically along the polydiene chain). A nickel catalyst modified by halogen compounds of nobornene is used. This method produces products containing, for example, per 1 mole of diene, 0.5 mole of aromatics and in some cases more than 70% of cis-1,4-double bonds.

German patent application No. P 28 48 804.2, corresponding to U.S. patent application Ser. No. 091,909, filed on Nov. 6, 1979, whose disclosures are incorporated by reference herein, relates to a process also producing reaction products of conjugated diolefins and aromatic hydrocarbons having a high percentage proportion of cis-1,4-double bonds and, as can be seen from its examples, only a minor portion ($\leq 1\%$) of 1,2-double bonds. In this process, not yet pertaining to the state of the art, conjugated diolefins are polymerized in an aromatic hydrocarbon using a catalyst consisting of a nickel compound soluble in the aromatic hydrocarbon, a halogen-containing organoaluminum compound, a selected modifier, and, optionally, water.

In U.S. Pat. Nos. 3,983,183 and 3,966,697, a P modified Co catalyst is disclosed as one component of a catalyst system used to polymerize conjugated dienes to form vinyl-containing polymers having low 1,4-trans-double bond contents.

SUMMARY OF THE INVENTION

It is an object of the present invention to provide a simple process permitting the preparation of reaction products of conjugated diolefins and aromatic hydrocarbons, the products having more than 1% 1,2- and less than 35% trans-1,4-double bonds in the polymer chain.

Upon further study of the specification and appended claims, further objects and advantages of this invention will become apparent to those skilled in the art.

These objects have been attained by providing a process for preparing a reaction product of a conjugated diolefin and an aromatic hydrocarbon comprising contacting these reactants with a catalyst comprising (1) a compound, soluble in the aromatic hydrocarbon, of a transition element with the VIIIth Group of the Periodic Table of the Elements;

(2) a halogen-containing organoaluminum compound; and (3) a modifier, wherein catalyst component (1) is a phosphorus-modified cobalt compound and catalyst component (3) is a compound of the formulae

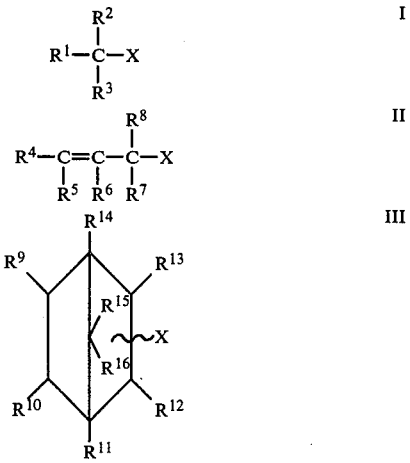

wherein
3.1 X is chlorine, bromine, or iodine, and
3.2 $R^1$ through $R^{16}$ are, independently of one another,
3.2.1 straight-chain or branched, saturated or unsaturated, aliphatic or cycloaliphatic hydrocarbon residues of 1-20 carbon atoms, optionally substituted by halogen atoms,
or
3.2.2 aryl residues of 6-14 carbon atoms optionally substituted by 1-5 straight-chain or branched, optionally halogen-substituted, saturated or unsaturated, aliphatic or cycloaliphatic hydrocarbon residues of 1-10 carbon atoms, and/or optionally substituted by halogen atoms, 3.2.3 and $R^2$ through $R^{16}$ can also be hydrogen, but $R^2$ and $R^3$ can be hydrogen only if $R^1$ is an aryl residue as defined in 3.2.2, and 3.2.4 $R^9$ and $R^{10}$ together can also form a condensed ring system which is optionally substituted.

DETAILED DISCUSSION

The results summarized above are surprising, since, under the reaction conditions, it was normally to be expected that a reaction would take place between the trivalent organic phosphorus compound used to modify the cobalt compound and the modifier. This reaction would be expected to be tantamount to an inhibition of the polymerization, or at least to an impairment of the course of the reaction.

Organic Phosphorus Compounds, Vol. 1, 1972, 79 ff., G. M. Kosolapoff and L. Maier; Houben-Weyl, Methoden der Organischen Chemie, Bd. Dec. 1, 1963, 79 ff. and Bd. Dec. 2, 1964 80 ff.

Suitable conjugated diolefins for use in the process of this invention are all 1,3-dienes conventionally used by the prior art (see, e.g., G. A. Olah, Friedel-Crafts and Related Reactions, vol. II/1, whose disclosures are incorporated by reference herein), such as, for example, butadiene, isoprene, piperylene, and 2,3-dimethyl-butadiene, butadiene being preferred.

All aromatic hydrocarbons which do not cause any undesired side reactions or cause only a minor acceptable degree of undesired side reactions under the reaction conditions can be utilized for reaction with the conjugated dienes, such as, for example, benzene, toluene, xylenes, chlorobenzene, cumene, or alkenyl aromatics, such as styrene and butenylbenzene. These generally have from 6 to 18 C atoms. Of course, mixtures of these can also be employed, as can mixtures containing in addition to the reactive aromatic hydrocarbon(s), hydrocarbons which do not react with the diene under the conditions utilized, such as, for example, hexane, heptane, octane, and cyclohexane.

In general, the conjugated diene is employed in a concentration of 1–50% by weight, based on the amount of the aromatic hydrocarbon. The concentration range from 5 to 40% by weight on the same basis is preferred.

Details of the phosphorous modified cobalt compound are conventional unless otherwise noted herein and, e.g., are given in U.S. Pat. Nos. 3,983,183 and 3,966,697, whose disclosures are incorporated by reference herein.

Suitable cobalt compounds for use in preparing catalyst component (1) include cobalt salts of organic and inorganic acids, as well as complex compounds of cobalt, e.g., cobalt chloride, cobalt bromide, cobalt iodide, cobalt sulfate, cobalt nitrate, cobalt carbonate, cobalt phosphate, cobalt sulfide, cobalt cyanide, cobalt cyanate, cobalt hydroxide, cobalt acetate, cobalt oxalate, cobalt octoate, cobalt naphthenate, cobalt stearate, cobalt palmitate, cobalt bis(acetyl)acetonate, cobalt bis-(aceto)acetate, dicyclopentadienyl cobalt, dicobalt octacarbonyl, etc. Preferred are cobalt octoate and cobalt bis(acetyl)acetonate.

The solubility of the cobalt compound in the aromatic hydrocarbon(s) should be 0.01–1 g Co/1 of the aromatic hydrocarbon before or after modification treatment with a trivalent organic phosphorus compound of the formula

wherein $R^{17}$, $R^{18}$, and $R^{19}$ each independently is $C_{1-14}$-alkyl, $C_{2-14}$-alkenyl, or $C_{6-14}$-aryl, or a group $OR^{20}$, $OR^{21}$, or $OR^{22}$, wherein $R^{20}$, $R^{21}$, and $R^{22}$, in turn, each independently is $C_{1-14}$-alkyl, $C_{2-14}$-alkenyl, or $C_{6-14}$-aryl.

Trivalent organic phosphorus compounds suitable for modifying the cobalt compounds include, on the one hand, alkyl, alkenyl, and aryl phosphines, and, on the other hand, phosphites having alkyl, alkenyl and/or aryl groups. In the phosphines, as well as in the phosphites, the hydrocarbon residues, which generally contain up to 14, preferably up to 10 carbon atoms, can be identical or different. Typical straight-chain, branched, or cyclic saturated or unsaturated aliphatic residues include, for example, methyl, ethyl, n-propyl, isopropyl, n-butyl, isobutyl, hexyl, octyl, cyclohexyl, vinyl, allyl, and crotyl. Typical aromatic residues include phenyl, toluyl, and benzyl.

Representative phosphines include triethyl, tri-n-butyl, triallyl, and triphenyl phosphine; representative phosphites include, trimethyl, triethyl, tripropyl, tributyl, tricyclohexyl, triallyl, triphenyl, diphenylethyl, diphenylallyl, diphenylbutyl, diethylphenyl, and dibutylphenyl phosphite. Preferred for purposes of the process of this invention are triphenyl phosphine, tri-n-butyl phosphine, and triphenyl phosphite.

Suitable halogen-containing organoaluminum compounds include those of the formula $R_nAlX_{3-n}$ wherein X is fluorine, chlorine, bromine, or iodine; R is an optionally substituted, aliphatic or aromatic hydrocarbon residue of up to 14 carbon atoms; and n is a whole or fractional number of 1 to 2. Preferably, R is an aliphatic hydrocarbon residue of 1–12, especially preferably of 1–4 carbon atoms. The residues R as well as the residues X can be alike or different.

Compounds usable within the range indicated for n, by themselves or in a mixture, are those of the general formulae $RAlX_2$, $R_{1.5}AlX_{1.5}$, and $R_2AlX$, wherein the methyl- and ethylaluminum halides are preferred. Especially preferred in the process of this invention are diethylaluminum chloride ($Et_2AlCl$), ethylaluminum dichloride ($EtAlCl_2$), and ethyl aluminum sesquichloride ($Et_{1.5}AlCl_{1.5}$).

Typical representatives of the modifiers usable in the process of this invention of Formula I are tertiary alkyl chlorides, bromides, and iodides, such as, for example, tert-butyl and amyl chloride, bromide, and iodide. Especially suitable are tert-butyl chloride and bromide, as well as tert-amyl chloride. Preferred such compounds when $R^1$ is aryl and the residues $R^2$ and $R^3$ are hydrogen include benzyl chloride and benzyl bromide.

Typical representatives of modifiers of Formula II include, for example, allyl, methallyl, and crotyl chloride, bromide, or iodide, wherein allyl chloride, allyl bromide, methallyl chloride, and crotyl chloride are especially preferred. It is not critical for the process of this invention whether the cis-form, the trans-form, or a mixture of isomers is involved.

Finally, among the modifiers of general Formula III, wherein the valences not illustrated in the formula are in all cases saturated by a hydrogen atom, typical representatives include: 2-chloro-, 2-bromo-, and 2-iodonorbornane-, 5-chloro-, 5-bromo-, and 5-iodo-2-norbornene, chloro-, bromo-, and iodotricyclo[5,2,1,0$^{2,6}$]- decane, 8(9)-chloro-, 8(9)-bromo-, and 8(9)-iodo-8,9-dihydrotricyclo[5,2,1,0$^{2,6}$]dec-3-ene. Especially suitable are 2-chloro-norbornane and 8(9)-chloro-8,9-dihydrotricyclo[5,2,1,0$^{2,6}$]dec-3-ene.

In the modifying agent component (3), when any of $R^1$ to $R^{16}$ independently are aliphatic or cycloaliphatic hydrocarbon radicals, the carbon atom content in each case preferably is 1–15, especially 3–12. Such radicals include alkyl, cycloalkyl, alkenyl, cycloalkenyl, alkynyl, etc. These radicals can optionally be substituted by 1–41, e.g., 1–30 halogen atoms of F, Cl, Br and I.

When any of $R^1$ to $R^{16}$ independently are aryl radicals, such aryl radicals are hydrocarbon including phenyl, naphthyl, anthryl, phenanthryl, etc. They may be substituted by 1–5, preferably 1–3, of the aliphatic or cycloaliphatic hydrocarbon radicals of 1–10, preferably 1–8, carbon atoms which are described above. They may also be substituted by 1–9 halogen atoms (F, Cl, Br, I). The aliphatic or cycloaliphatic hydrocarbon radical substituents, in turn, may be substituted by 1–15 halogen atoms (F, Cl, Br, I).

In formula III, $R^9$ and $R^{10}$ together can also be constituents of a fused-on ring system, thereby forming equivalent moieties. The fused-on ring (or ring system) may optionally be substituted.

As a result, the modifiers include examples such as 2-chloro-, 2-bromo-, and 2-iodonorbornane-, 5-chloro-, 5-bromo-, and 5-iodo-2-norbornene, chloro-, bromo-, and iodotricyclo[5,2,1,0$^{2,6}$]-decane, 8(9)-chloro-, 8(9)-bromo-, and 8(9)-iodo-8,9-dihydrotricyclo[5,2,1,0$^{2,6}$]-dec-3-ene.

$R^4$ to $R^{16}$ can alternatively be hydrogen, and $R^1$ and $R^2$ can also be hydrogen when $R^3$ is optionally substituted hydrocarbon aryl as defined.

Besides the aforementioned ingredients, the catalyst can optionally contain, as catalyst component (4), an H-acidic compound, such as water, alcohols, or organic acids.

The cobalt compound is generally utilized in amounts of 0.01–1 mole, based on 1 mole of the halogen-containing organo-aluminum compound (2). Preferred is 0.02–0.5 mole, based on 1 mole of (2).

The proportion of trivalent organic phosphorus compound utilized for modifying the cobalt compound amounts generally to 0.1–50 moles, preferably 0.3–10 moles, based on 1 mole of cobalt compound.

The halogen-containing organoaluminum compound (2) is generally utilized in an amount of 0.0005 to 0.02 mole, based on 1 mole of the conjugated diene. An amount of 0.001–0.01 mole is preferred.

Finally, the modifier (3) is generally employed in an amount of 0.01–20 moles, preferably 0.1–5 moles, based on 1 mole of the halogen-containing organoaluminum compound.

Insofar as the catalyst also has an H-acidic compound added thereto, it is contained in a quantity of 0.05–10 moles, preferably 0.1–1 mole, based on 1 mole of the halogen-containing organoaluminum compound.

The process of this invention is advantageously conducted in an apparatus whereby a rather vigorous temperature and pressure increase can be controlled without danger, i.e., wherein the diene can be added continuously or in incremental portions even under increasing pressure. These conditions are met, for example, by an autoclave. The reaction, however, can also be carried out in batchwise operation with a one-time addition of diene, for example in a reaction flask or in a high-pressure tubular reactor.

The reaction temperature can be varied within a wide range, e.g., from −50° to +200° C., but the temperature range from −20° to +130° C. is preferred; especially preferred is the range from −10° to +100° C. The reaction pressure is generally up to 30 bar; the reaction time is generally 0.1 to 5 hours.

The reaction products produced according to the process of the invention can be worked up and purified, for example, by first deactivating the catalyst with the necessary quantity of, e.g., water, alcohol, or acetone. The reaction batch is then stirred first of all, for example, with bleaching clay and, optionally, an alkaline compound, such as sodium carbonate, potassium carbonate, or calcium oxide; and then the batch is subjected to filtration. If esters of phosphorous acid were utilized as organic phosphorus compounds which are to be removed from the reaction product, this can be done by a treatment with superheated steam or hot water.

The amount of bleaching (active) clay added is determined by the catalyst concentration and the size of the batch. An adequate amount to be added can readily be found by orientation experiments as are fully conventional.

The excess solvent is then distilled off, optionally after adding a stabilizer, such as, for example, 2,6-di-tert-butyl-p-cresol. Methods which can be used for this working-up step include not only the classical, conventional procedures, but also, for example, distillation removal on a thin-film evaporator. In this connection, if desired, low-boiling reaction products can also be distilled off. It is possible, especially in the case of higher-molecular weight products, to isolate the reaction products by adding a precipitant effecting phase separation. In this connection, fractionation can take place. Suitable precipitants are, for example, water and/or methanol, ethanol, acetone, etc.

In the above-described manner, products can be obtained having a broad spectrum of properties, for example having viscosities of 30 to $10^5$ mPa·s, but also solid polymers; and having iodine numbers of 50 to the range of the pure polydiolefins.

The proportion of 1,2- or vinyl double bonds in the reaction products prepared according to the process of this invention can be varied within a wide range. This proportion is in all cases more than 1% and generally is 5% to 30%. The remaining double bonds are to be predominantly of a cis-1,4-configuration and maximally to an extent of 35% of a trans-1,4-configuration.

A control of the aryl group incorporation is possible by adapting the reaction conditions and is determined in the simplest way spectroscopically by the presence of substituted aromatics and the proportion of aromatic protons. The latter is, on the average, between 3% and 25%, based on the total proportion of protons.

Details of the polymerization using the catalyst of this invention, unless otherwise noted herein, are fully conventional, e.g., as disclosed in U.S. Pat. Nos. 3,983,183 and 3,966,697 as well in German patent application No. P 28 48 804.2, corresponding to U.S. patent application Ser. No. 091,909, filed on Nov. 6, 1979, whose disclosure is incorporated by reference herein.

The reaction products obtained according to the process of this invention are especially well suited to the preparation of nonpolluting, air-drying coatings, optionally after preceding modification, such as, for example, maleic anhydride addition, halogenation, hydrogenation, etc. See, e.g., U.S. Pat. No. 3,546,184, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The characteristic values indicated in the examples were determined as follows:

1. Iodine number: M. E. Tunnicliffe et al., European Polym. J. (1965) 1:260.
2. NMR (Microstructure and proton distribution): E. Pretsch et al., "Tabellen zur Strukturaufklaerung org. Verbindungen" [Tables for Clarifying the Structure of Organic Compounds], Springer publishers, 1976.
3. IR: P. Simák and G. Fahrbach, "Angew. Makromol. Chem." [Applied Macromolecular Chemistry] (1970) 12:73–88.
4. Raman: B. Schrader, "Angewandte Chemie" [Applied Chemistry] (1973) 85:925.

EXAMPLE 1

A 2.5-liter glass autoclave with double jacket and lateral tube was charged with 1.7 l of toluene of a temperature of 30° C., dried over a molecular sieve, and 125 g of dry butadiene. Thereafter, the following ingredients were added in succession: 0.75 millimole of cobalt octoate (as a 0.1-molar solution in toluene), 1.5 mmol of triphenyl phosphite (1-molar in toluene), 20 mmol of diethylaluminum chloride (1-molar in toluene), and 11 mmol of water. After the internal temperature had risen by 5°, 8 mmol of 5-chloro-2-norbornene was added and, quickly, another 125 g of butadiene was introduced into the reaction mixture. The temperature rose to 59° C. during this step.

After a reaction time of 2 hours at 50° C., the toluene solution was drained off, deactivated with methanol, and then about 20 g of sodium carbonate monohydrate and 30 g of bleaching clay were added and the mixture filtered. After the solvent, toluene, had been distilled off at 120° C., under vacuum, there remained 223 g of a light-yellow oil having a viscosity of 500 mPa·s and an iodine number of 268. The double bond content, determined by IR spectroscopy, was 12% 1,2-; 24% trans-1,4-; and 64% cis-1,4-units. From the $^1$H-NMR spectrum, 12.4% aromatic and 19.7% olefinic protons were calculated.

EXAMPLE 2

The procedure of Example 1 was followed, but the reagents were added at 50° C. in the sequence of: 1.7 l of dry toluene, 11 mmol of water, 125 g of butadiene, 20 mmol of $(C_2H_5)_2AlCl$, 8 mmol of 2-methylallyl chloride, 1.5 mmol of triphenyl phosphite, 0.75 mmol of cobalt octoate, and, thereafter, another 125 g of butadiene.

The internal temperature rose to 84° C. After the mixture had been worked up, 233 g of an oil was obtained having a viscosity of 2,100 mPa·s and an iodine number of 227. The double bond content was 5%, 1,2-, 26% trans-1,4-, and 69% cis-1,4-units.

The $^1$H-NMR spectrum showed 16% aromatic and 15.3% olefinic protons.

COMPARATIVE EXAMPLE A 250 g of butadiene was introduced into a solution of the preformed catalyst, consisting of 1 mmol of cobalt octoate, 5 mmol of tri-n-butyl phosphine, and 10 mmol of $Et_3Al_2Cl_3$—dissolved in 2 l of dry toluene of 50° C. The reaction temperature rose to maximally 80° C.; the reaction time was 2 hours.

After the reaction mixture had been worked up as described in Example I, 110 g of highly viscous polybutadiene was obtained, having an iodine number of 454. The viscosity was 2,500 mPa·s. By IR spectroscopy, 35% 1,2-, 8% trans-1,4-, and 57% cis-1,4- double bonds were detected. In the $^1$H-NMR spectrum, only 0.4% of aromatic protons was found, in addition to 39.4% olefinic and 60.2% aliphatic protons. The residual toluene content was 0.33%.

The example demonstrates that, without the addition of a chlorinated hydrocarbon as the modifier according to this invention, no appreciable incorporation of aryl groups took place.

COMPARATIVE EXAMPLE B

The procedure of Comparative Example A was followed, but 10 mmol of the 1-chlorobutane was added after preforming of the catalyst. The internal temperature during polymerization rose from 50° C. to maximally 82° C. Yield: 95 g of a highly viscous polybutadiene oil having a viscosity of $10^4$ mPa·s and an iodine number of 446. This product had a microstructure, determined by IR spectroscopy, of 35%, 1,2-, 10% trans-1,4-, and 55% cis-1,4-double bonds. In the $^1$H-NMR spectrum, with a residual toluene content of <1%, less than 0.5% aromatic protons were detected.

The example shows that, when using a halogenated hydrocarbon not covered by Formulae I through III, no appreciable incorporation of aryl groups is achieved.

EXAMPLES 3–9

The procedure of Example I was followed. Insofar as modifications were made, these are listed in the following table, together with the test results. Cobalt octoate was used in all instances as the cobalt compound.

TABLE

| Example No. | Type and Amount (mmol) of Catalyst Components | | | Type and Amount (mmol) of Modifier | Yield (g) | Starting Temp. (°C.) | Maximum Temp. (°C.) | Reaction Time (min) | Viscosity (mPa. s) |
| --- | --- | --- | --- | --- | --- | --- | --- | --- | --- |
| | Co Compd. | P Compd. | Org—Al Compd. | | | | | | |
| 3 | 0.75 | P (OPh)$_3$ 1.5 | Et$_3$Al$_2$Cl$_3$ 10 | A (1) 8.0 | 146 | 35 | 68 | 30 | 2,500 |
| 4 | 0.75 | PPh$_3$ 3.75 | Et$_3$Al$_2$Cl$_3$ 10 | 2-Methylallyl chloride 8.0 | 168 | 50 | 104 | 60 | 25,000 |
| 5 | 0.75 | PPh$_3$ 3.75 | Et$_3$Al$_2$Cl$_3$ 10 | 2-Methylallyl chloride 8.0 | 258 | 50 | 112 | 60 | 8,000 |

TABLE-continued

| | | | | | | | | |
|---|---|---|---|---|---|---|---|---|
| 6 | 0.75 | P(C$_4$H$_9$—n)$_3$ 3.75 | Et$_3$Al$_2$Cl$_3$ 10 | A(1) 8.0 | 225 | 30 | 99 | 15 | 39,000 |
| 7 | 1.0 | P(C$_4$H$_9$—n)$_3$ 5.0 | Et$_2$AlCl plus 11.1 mmol H$_2$O 20 | A(1) 8.0 | 203 | 50 | 102 | 40 | 22,000 |
| 8 | 1.0 | P(C$_4$H$_9$—n)$_3$ 5.0 | EtAlCl$_2$ 20 | A(1) 8.0 | 245 | 30 | 110 | 30 | 28,000 |
| 9 | 1.0 | P(OPh)$_3$ 2.0 | EtAlCl$_2$ 20 | A(1) 10 | 380 | 45 | 140 | 30 | 230 |

| Example No. | Iodine Number | Microstructure (%) | | | Residual Toluene (% by Wt.) | Proton Distribution (%) | | | | Remarks |
|---|---|---|---|---|---|---|---|---|---|---|
| | | cis-1,4 | trans-1,4 | 1,2 | | aromat. (2) | olef. | benzyl | aliph. (3) | |
| 3 | 281 | 68 | 24 | 8 | <0.01 | 9.7 | 20.8 | 5.0 | 64.5 | Without H$_2$O as catalyst component |
| 4 | 307 | 67 | 19 | 14 | 5.2 | 5.0 | 22.1 | 2.0 | 67.7 | Without H$_2$O as catalyst component |
| 5 | 176 | n.e (4) | 15 (5) | 3 (5) | <0.1 | 15.2 | 9.6 | 3.9 | 70.1 | Without H$_2$O as catalyst component |
| 6 | 379 | 65 | 16 | 19 | <0.05 | 3.9 | 29.6 | 1.6 | 64.9 | Without H$_2$O as catalyst component |
| 7 | 361 | 63 | 16 | 21 | 0.76 | 4.6 | 28.9 | 2.7 | 63.3 | Total amount of butadiene charged; 10 mmol Et$_3$Al$_2$Cl$_3$ added 1 min. after butadiene metering |
| 8 | 240 | 67 | 25 | 8 | 0.51 | 11.8 | 15.7 | 4.7 | 67.5 | Total amount of butadiene charged, without H$_2$O as catalyst component |
| 9 | 186 | n.e (4) | 17 (5) | 2 (5) | — | — | — | — | — | Total amount of butadiene charged, without H$_2$O as catalyst component |

(1) A = 8 (9)-Chloro-8,9-dihydrodicyclopentadiene
(2) Considering the residual toluene content
(3) Including the methyl protons of toluene
(4) Cannot be evaluated
(5) Absolute values The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a reaction product of a conjugated diolefin and an aromatic hydrocarbon comprising contacting these reactants with a catalyst comprising (1) a phosphorous modified cobalt compound comprising a cobalt compound which is soluble in the aromatic hydrocarbon, and a phosphorus compound of the formula

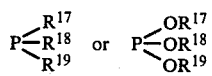

wherein R$^{17}$, R$^{18}$ and R$^{19}$ each, independently, is C$_{1-14}$-alkyl, C$_{2-14}$-alkenyl or C$_{6-14}$-aryl;

(2) a halogen-containing organoaluminum compound; and (3) a modifier of the formula

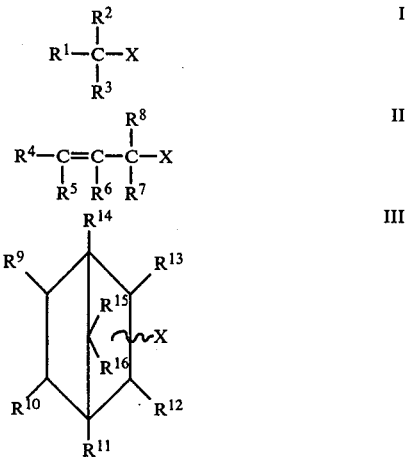

wherein
X is chlorine, bromine, or iodine, and
R$^1$ through R$^{16}$, independently are
straight-chain or branched, saturated or unsaturated, aliphatic or cycloaliphatic hydrocarbon radicals of 1–20 carbon atoms, optionally substituted by 1–41 halogen atoms, or
hydrocarbon aryl radicals of 6–14 carbon atoms optionally substituted by (a) 1–5 straight-chain or branched, saturated or unsaturated, aliphatic or cycloaliphatic hydrocarbon radicals each of 1–10 carbon atoms, each optionally halogen-substituted, or (b) 1–9 halogen atoms and wherein $R^4$ through $R^{16}$ can also be hydrogen, and $R^2$ and $R^3$ can also be hydrogen only when $R^1$ is optionally substituted hydrocarbon aryl as defined above.

2. A process of claim 1, wherein the catalyst further comprises an H-acidic compound which is water, an alcohol or an organic acid.

3. A process of claim 2, wherein the H-acidic compound is water.

4. A process of claim 1, wherein the cobalt compound is cobalt octoate or cobalt bis(acetyl) acetonate.

5. A process of claim 1, wherein the phsophorous compound is triphenyl phosphine, tri-n-butyl phosphine or triphenyl phosphite.

6. A process of claim 1, wherein the halogen-containing organoaluminum compound is of the formula $R_nAlX_{3-n}$, wherein n is a whole or fractional number of 1-2, X is F, Cl, Br or I and R is a hydrocarbon radical of 1-14 C atoms.

7. A process of claim 1, wherein the modifier is a tertiary alkyl chloride, bromide or iodide of 4 or 5 carbon atoms or benzyl chloride or bromide.

8. A process of claim 1, wherein the modifier is allyl, methallyl or crotyl chloride, bromide or iodide.

9. A process of claim 1, wherein the modifier is 2-chloro-, 2-bromo-, or 2-iodonorbornane-; 5-chloro-, 5-bromo-, or 5-iodo-2-norbornene; chloro-, bromo-, or iodotricyclo[5,2,1,0$^{2,6}$]-decane; or 8(9)-chloro-, 8(9)-bromo-, or 8(9)-iodo-8,9-dihydrotricyclo[5,2,1,0$^{2,6}$]dec-3-ene.

10. A process of claim 1, wherein the amounts of components are as follows:
   conjugated diolefin: 1–50% by weight based on the weight of the aromatic hydrocarbon reactant;
   cobalt compound: 0.01–1 mole per 1 mole of halogen-containing organoaluminum compound;
   phosphorous compound: 0.1–50 moles, per 1 mole of cobalt compound;
   halogen-containing organoaluminum compound: 0.0005–0.02 mole per 1 mole of conjugated diolefin; and
   modifier: 0.01–20 moles per 1 mole of halogen-containing organoaluminum compound.

11. A process of claim 10, wherein the catalyst further comprises
   0.05–10 moles of H-acid compound per 1 mole of halogen-containing organoaluminum compound.

12. A process of claim 1, wherein the modifier is of the formula I or II or is chloro-, bromo-, or iodotricyclo[5,2,1,0$^{2,6}$]-decane; or 8(9)-chloro-, 8(9)-bromo-, or 8(9)-iodo-8,9-dihydrotricyclo[5,2,1,0$^{2,6}$]dec-3-ene.

* * * * *